(12) United States Patent
Amano et al.

(10) Patent No.: US 11,166,621 B2
(45) Date of Patent: Nov. 9, 2021

(54) MEDICAL APPARATUS AND METHOD OF MANUFACTURING MEDICAL APPARATUS

(71) Applicant: Sony Olympus Medical Solutions Inc., Tokyo (JP)

(72) Inventors: Kohtaro Amano, Tokyo (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/490,079

(22) PCT Filed: Oct. 25, 2017

(86) PCT No.: PCT/JP2017/038576
§ 371 (c)(1),
(2) Date: Aug. 30, 2019

(87) PCT Pub. No.: WO2018/163498
PCT Pub. Date: Sep. 13, 2018

(65) Prior Publication Data
US 2020/0029790 A1     Jan. 30, 2020

(30) Foreign Application Priority Data
Mar. 8, 2017    (JP) .............................. JP2017-044213

(51) Int. Cl.
*A61B 1/00*          (2006.01)
*A61B 1/04*          (2006.01)
(Continued)

(52) U.S. Cl.
CPC ........ *A61B 1/00009* (2013.01); *A61B 1/0011* (2013.01); *A61B 1/00114* (2013.01);
(Continued)

(58) Field of Classification Search
CPC .............. A61B 1/00009; A61B 1/0011; A61B 1/00114; A61B 1/00117; A61B 1/00126;
(Continued)

(56) References Cited

U.S. PATENT DOCUMENTS 6,945,704 B2 *   9/2005   Yamaguchi .......... G02B 6/3869
                                                   385/60
8,942,530 B2     1/2015   Demers et al.
(Continued)

FOREIGN PATENT DOCUMENTS

| CN | 101833131 A | 9/2010 |
|---|---|---|
| CN | 102948141 A | 2/2013 |

(Continued)

OTHER PUBLICATIONS

Extended European Search Report dated Feb. 4, 2020, issued in corresponding European Patent Application No. 17900201.9.
(Continued)

*Primary Examiner* — Loi H Tran
(74) *Attorney, Agent, or Firm* — Xsensus LLP

(57) ABSTRACT

A medical apparatus and a method of manufacturing the medical apparatus, which have an advantage in cost performance, are provided even if optical fibers are used therein. The medical apparatus includes, therein, a first optical fiber 6322 configured to transmit an optical signal, a second optical fiber 651 configured to transmit an optical signal, and a first optical connector 66 configured to connect the first optical fiber 6322 and the second optical fiber 651.

20 Claims, 14 Drawing Sheets

(51) Int. Cl.
*H04N 7/18* (2006.01)
*H04N 7/22* (2006.01)

(52) U.S. Cl.
CPC ...... *A61B 1/00117* (2013.01); *A61B 1/00126* (2013.01); *A61B 1/00165* (2013.01); *A61B 1/04* (2013.01); *H04N 7/183* (2013.01); *H04N 7/22* (2013.01)

(58) Field of Classification Search
CPC ... A61B 1/00165; A61B 1/04; A61B 1/00124; A61B 1/00013; A61B 1/00018; A61B 1/051; A61B 1/00; H04N 7/183; H04N 7/22; G02B 6/389; G02B 6/3877; G02B 23/24
USPC .......................................................... 348/75
See application file for complete search history.

(56) References Cited

U.S. PATENT DOCUMENTS

| | | | | |
|---|---|---|---|---|
| 9,904,020 | B2* | 2/2018 | Akieda | G02B 6/3885 |
| 2003/0070257 | A1* | 4/2003 | Takahashi | G02B 6/3835 |
| | | | | 16/108 |
| 2007/0237471 | A1 | 10/2007 | Aronson | |
| 2010/0329609 | A1* | 12/2010 | Shimotsu | G02B 6/32 |
| | | | | 385/50 |
| 2010/0331626 | A1* | 12/2010 | Shimotsu | A61B 1/00126 |
| | | | | 600/182 |
| 2013/0012777 | A1* | 1/2013 | Baum | A61B 1/00029 |
| | | | | 600/110 |
| 2013/0216186 | A1* | 8/2013 | Ott | G02B 6/3863 |
| | | | | 385/70 |
| 2013/0272664 | A1* | 10/2013 | Arao | G02B 6/43 |
| | | | | 385/89 |
| 2014/0321813 | A1* | 10/2014 | Lu | G02B 6/3887 |
| | | | | 385/78 |
| 2016/0029874 | A1* | 2/2016 | Usami | A61B 1/045 |
| | | | | 600/110 |
| 2016/0206185 | A1* | 7/2016 | Kinouchi | A61B 1/00009 |
| 2016/0316995 | A1 | 11/2016 | Michihata | |
| 2017/0049301 | A1 | 2/2017 | Hagihara et al. | |
| 2019/0290104 | A1* | 9/2019 | Culman | A61B 1/00057 |
| 2020/0064561 | A1* | 2/2020 | Alrutz | G02B 6/3874 |

FOREIGN PATENT DOCUMENTS

| | | |
|---|---|---|
| EP | 2543309 A | 1/2013 |
| JP | 2004-202040 A | 7/2004 |
| JP | 2005181902 A | 7/2005 |
| JP | 2013-33158 A | 2/2013 |
| JP | 2016071205 A | 5/2016 |
| WO | 2012/033200 A1 | 3/2012 |
| WO | 2014/171332 A1 | 10/2014 |
| WO | 2016/002415 A1 | 1/2016 |
| WO | WO-2016098419 A | 6/2016 |
| WO | 2016/147556 A1 | 9/2016 |
| WO | WO-2016147556 A1 | 9/2016 |
| WO | 2016/170838 A1 | 10/2016 |
| WO | WO-2016170838 A | 10/2016 |

OTHER PUBLICATIONS

International Search Report and Written Opinion dated Jan. 23, 2018 for PCT/JP2017/038576 filed on Oct. 25, 2017, 10 pages including English Translation of the International Search Report.

* cited by examiner

MEDICAL APPARATUS AND METHOD OF MANUFACTURING MEDICAL APPARATUS

CROSS-REFERENCE TO RELATED APPLICATIONS

The present application is based on PCT filing PCT/JP2017/038576, filed Oct. 25, 2017, which claims priority to JP 2017-044213, filed Mar. 8, 2017, the entire contents of each are incorporated herein by reference.

TECHNICAL FIELD

The present invention relates to a medical apparatus and a method of manufacturing the medical apparatus.

BACKGROUND ART

Recently known is a technique for performing transmission by using an optical fiber as a transmission cable for high speed transmission of a large volume of image signals to an image processing device, due to increase in the numbers of pixels of an imaging device, such as a complementary metal oxide semiconductor (CMOS), in a medical apparatus, such as an endoscope (see Patent Literature 1). According to this technique, by provision of an E/O converter, which converts an image signal (an electric signal) generated by the imaging device into an optical signal, at a distal end side of the optical fiber, and provision of an O/E converter, which converts an optical signal into an image signal, at a proximal end side of the optical fiber; a large volume of image signals generated by the imaging device is transmitted to the image processing device at high speed.

CITATION LIST

Patent Literature

Patent Literature 1: International Publication WO 2012/033200

DISCLOSURE OF INVENTION

Technical Problem

Because the optical fiber is very thin and its core that transmits the optical signal has a very thin diameter, advanced skills are required in the work of aligning the optical axis with that of the E/O converter or the O/E converter. Therefore, the work of aligning the optical axes is desirably carried out respectively by converter manufacturers of the E/O converter and O/E converter. However, if the optical fiber is supplied from the optical fiber manufacturer to a converter manufacturer, transportation cost for the supply is needed and disconnection of the optical fiber may occur when the optical fiber is supplied. Furthermore, in a case where a converter manufacturer connects, to the optical fiber already connected with one of the E/O converter and O/E converter, the other converter, disconnection of the optical fiber may occur due to the load from the one of the E/O converter and O/E converter. Due to such multiple factors, it has been difficult to say that use of optical fibers in medical apparatuses is economical.

The present invention has been made in view of the above, and an object thereof is to provide: a medical apparatus and a method of manufacturing the medical apparatus, which are highly economical even if optical fibers are used therein.

Solution to Problem

To solve the above-described problem and achieve the object, a medical apparatus according to the present invention includes, therein: a first optical fiber configured to transmit an optical signal; a second optical fiber configured to transmit the optical signal; and an optical connector configured to connect the first optical fiber and the second optical fiber.

Moreover, the above-described medical apparatus according to the present invention further includes, therein, at least one of: an E/O converter to which the first optical fiber is connected, the E/O converter being configured to convert an electric signal into the optical signal; and an O/E converter to which the second optical fiber is connected, the O/E converter being configured to convert the optical signal into an electric signal.

Moreover, the above-described medical apparatus according to the present invention further includes a composite cable including: a metal cable configured to transmit an electric signal; and at least one of the first optical fiber and the second optical fiber, the metal cable and the at least one of the first optical fiber or the second optical fiber having been formed into a unit.

Moreover, the above-described medical apparatus according to the present invention further includes a sheath configured to cover the composite cable.

Moreover, the above-described medical apparatus according to the present invention further includes: a substrate; and a cable connector provided on the substrate and configured to connect the substrate and the metal cable.

Moreover, in the above-described medical apparatus according to the present invention, the medical apparatus is an endoscope apparatus.

Moreover, in the above-described medical apparatus according to the present invention, the medical apparatus is an endoscope camera head.

Moreover, in the above-described medical apparatus according to the present invention, the medical apparatus is a surgical microscope.

Moreover, in the above-described medical apparatus according to the present invention, the medical apparatus is a transmission cable that has one end connected to an endoscope camera head and another end connected to an image processing device, and is configured to transmit an image signal from the endoscope camera head to the image processing device, the image signal serving as the optical signal.

Moreover, a method of manufacturing a medical apparatus according to the present invention includes: a first optical fiber that transmits an optical signal; a second optical fiber that transmits the optical signal; and a connection process of connecting the first optical fiber and the second optical fiber to each other by using an optical connector.

Advantageous Effects of Invention

According to the present invention, an effect of being highly economical even if an optical fiber is used is achieved.

BEST MODE FOR CARRYING OUT THE INVENTION

Hereinafter, modes for carrying out the present invention will be described in detail, together with the drawings. The present invention is not limited by the following embodiments. Furthermore, the drawings referred to in the following description schematically illustrate shapes, sizes, and positional relations merely to an extent that allows substance of the present invention to be understood. That is, the present invention is not limited only to the shapes, sizes, and positional relations exemplified by the drawings. Moreover, any portions that are same will be assigned with the same reference sign throughout the drawings.

First Embodiment

Schematic Configuration of Medical Apparatus

Figure 1:
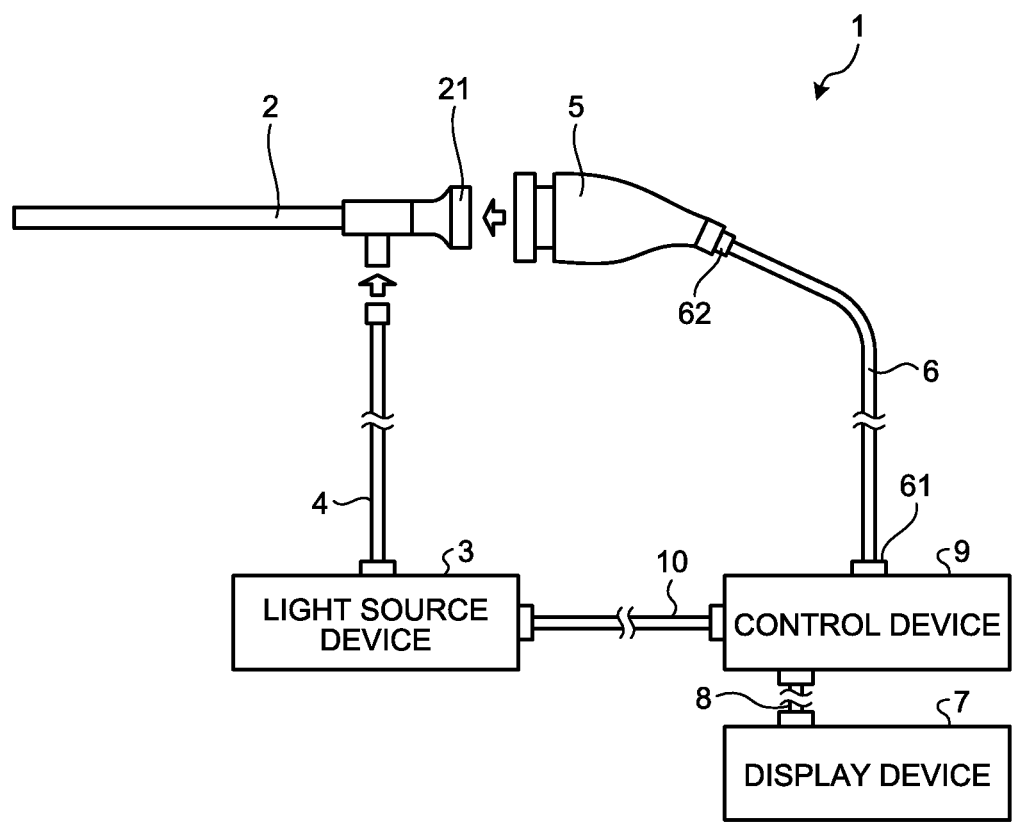
FIG. 1 is a diagram illustrating a schematic configuration of a medical apparatus according to a first embodiment of the present invention.

FIG. 1 is a diagram illustrating a schematic configuration of a medical apparatus according to a first embodiment of the present invention.

A medical apparatus 1 illustrated in FIG. 1 is an apparatus used in the medical field and for observation of the interior of a subject, such as a living body. A rigid endoscope having, used therein, a rigid scope (an insertion unit 2) illustrated in FIG. 1 will be described as the medical apparatus 1 according to the first embodiment, but the medical apparatus 1 may be a flexible endoscope, without being limited to the rigid endoscope.

As illustrated in FIG. 1, the medical apparatus 1 includes the insertion unit 2, a light source device 3, a light guide 4, an endoscope camera head 5 (an endoscopic imaging device), a first transmission cable 6, a display device 7, a second transmission cable 8, a control device 9, and a third transmission cable 10.

The insertion unit 2 is rigid, or at least a part thereof is flexible, and the insertion unit 2 has an elongated shape and is inserted into a subject, such as a patient. Provided inside the insertion unit 2 is an optical system, which is formed by use of one or plural lenses and forms an observation image.

The light source device 3 is connected with one end of the light guide 4, and supplies, under control by the control device 9, light for illuminating the interior of the subject, to the one end of the light guide 4. The light source device 3 is formed by use of, for example, a light emitting diode (LED) lamp or a halogen lamp.

The one end of the light guide 4 is attachably and detachably connected to the light source device 3, and the other end of the light guide 4 is attachably and detachably connected to the insertion unit 2. By transmitting the light supplied from the light source device 3 from the one end to the other end, the light guide 4 supplies the light to the insertion unit 2.

An eyepiece unit 21 of the insertion unit 2 is attachably and detachably connected to the endoscope camera head 5. Under control by the control device 9, the endoscope camera head 5 captures the observation image formed by the insertion unit 2, converts this imaging signal (an electric signal) to an optical signal, and outputs the optical signal.

One end of the first transmission cable 6 is attachably and detachably connected to the control device 9 via a video connector 61, and the other end thereof is connected to the endoscope camera head 5 via a camera head connector 62. The first transmission cable 6 transmits the imaging signal output from the endoscope camera head 5, to the control device 9, and transmits each of a control signal, a synchronization signal, a clock, power, and the like that are output from the control device 9, to the endoscope camera head 5. A detailed configuration of the first transmission cable 6 will be described later.

Under control by the control device 9, the display device 7 displays thereon an observation image based on a video signal processed by the control device 9 and various information related to the medical apparatus 1. The display device 7 is formed by use of liquid crystal, organic electroluminescence, or the like.

One end of the second transmission cable 8 is attachably and detachably connected to the display device 7, and the other end thereof is attachably and detachably connected to the control device 9. The second transmission cable 8 transmits the video signal processed by the control device 9, to the display device 7.

The control device 9 is configured to include a central processing unit (CPU), a graphics processing unit (GPU), various memories, and the like, and integrally controls operation of the light source device 3, the endoscope camera head 5, and the display device 7, via the first transmission cable 6, the second transmission cable 8, and the third transmission cable 10, according to a program recorded in a memory (not illustrated in the drawings). According to this first embodiment, the control device 9 functions as an image processing device.

One end of the third transmission cable 10 is attachably and detachably connected to the light source device 3, and the other end thereof is attachably and detachably connected to the control device 9. The third transmission cable 10 transmits the control signal from the control device 9 to the light source device 3.

Configuration of First Transmission Cable

Described next is a configuration of the first transmission cable 6.

Figure 2:
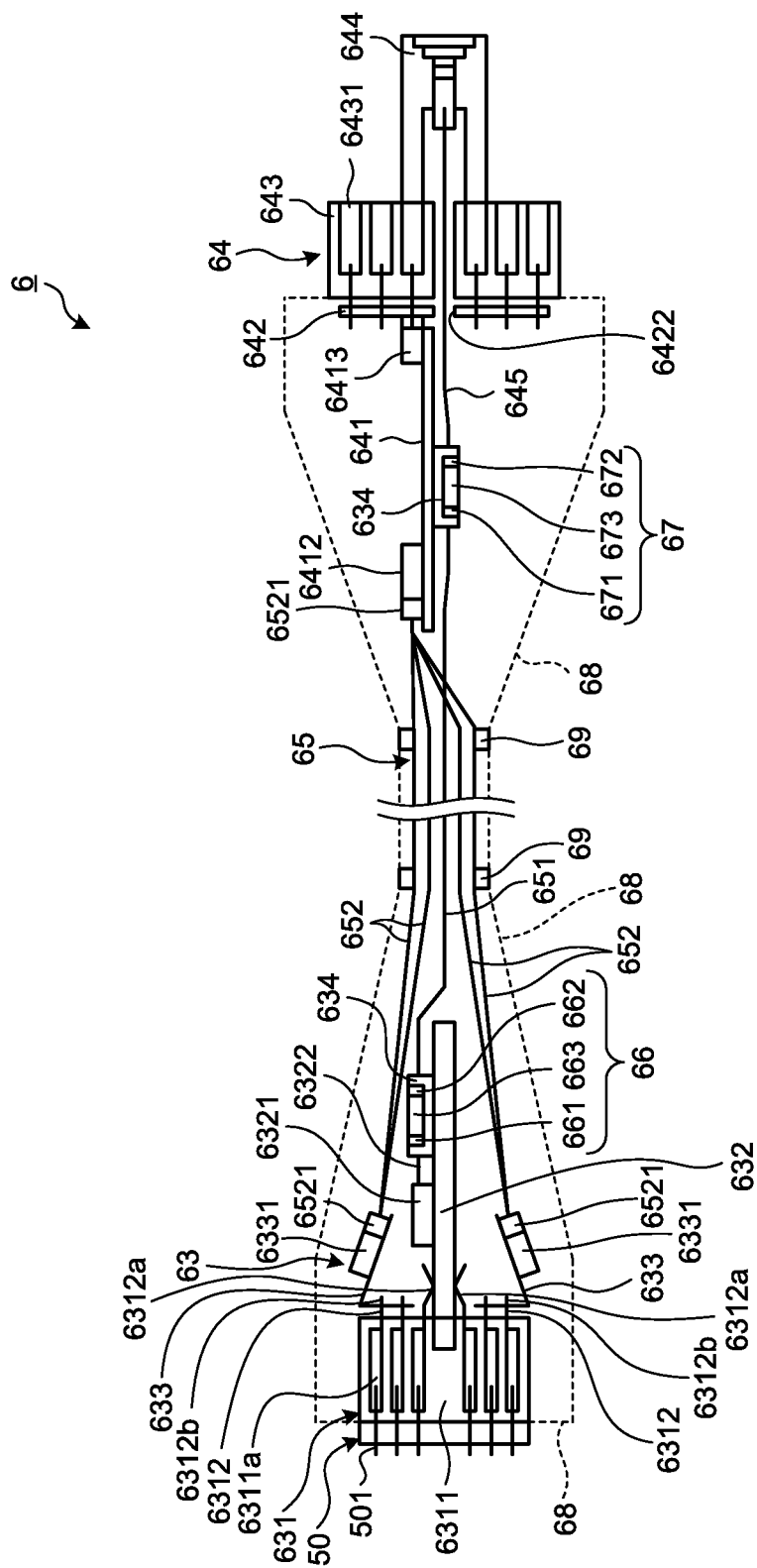
FIG. 2 is a schematic diagram illustrating a cross section of a first transmission cable according to the first embodiment of the present invention.
Figure 3:
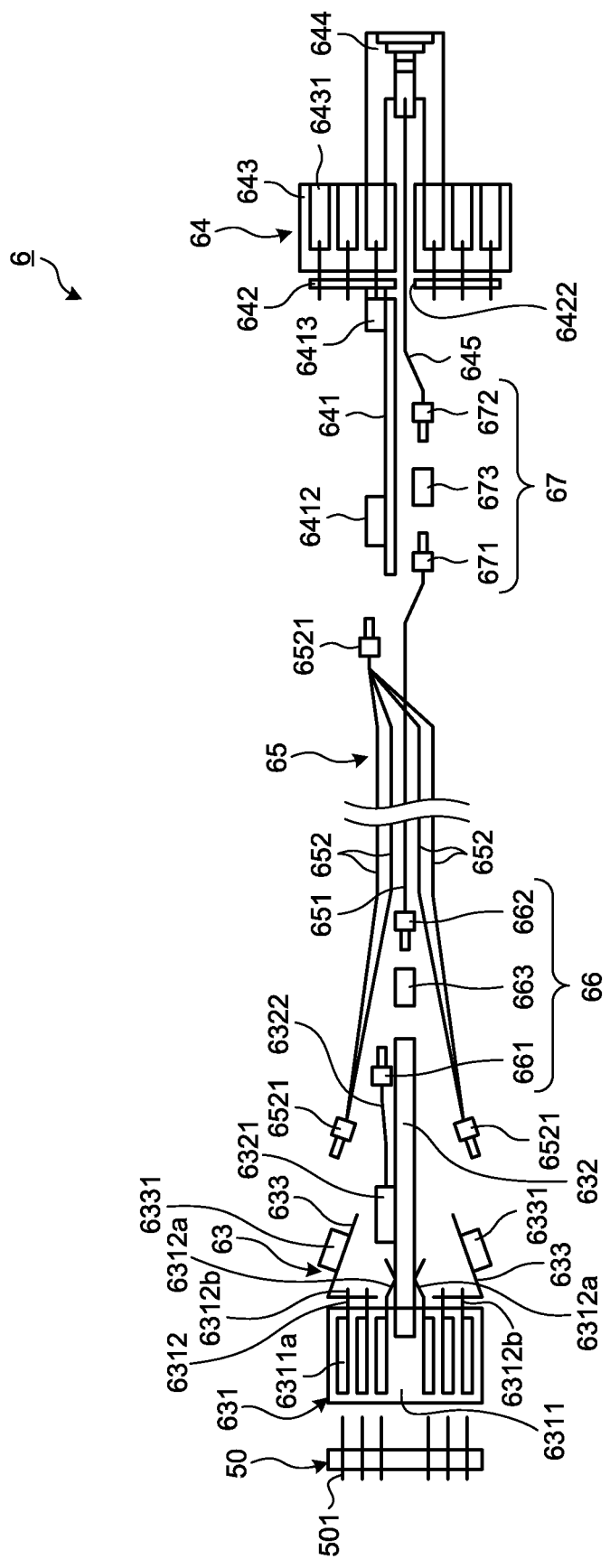
FIG. 3 is a schematic diagram illustrating a cross section of main parts of the first transmission cable according to the first embodiment of the present invention.

FIG. 2 is a schematic diagram illustrating a cross section of the first transmission cable 6. FIG. 3 is a schematic diagram illustrating a cross section of main parts of the first transmission cable 6.

As illustrated in FIG. 2 and FIG. 3, the first transmission cable 6 includes: a first photoelectric composite module 63 provided in the camera head connector 62; a second photoelectric composite module 64 provided in the video connector 61; a composite cable 65 optically and electrically connecting the first photoelectric composite module 63 and the second photoelectric composite module 64 to each other; first optical connectors 66, which optically connect the first photoelectric composite module 63 and the composite cable 65 to each other; second optical connectors 67, which optically connect the second photoelectric composite module 64 and the composite cable 65 to each other; and a sheath 68 (an outer wall), which covers the first photoelectric composite module 63, the second photoelectric composite module 64, the composite cable 65, the first optical connectors 66, and the second optical connectors 67, and is flexible.

Configuration of First Photoelectric Composite Module

Firstly described is the first photoelectric composite module 63.

The first photoelectric composite module 63 is mechanically and electrically connected to a hermetic connector 50 provided in the endoscope camera head 5. The first photoelectric composite module 63 converts an imaging signal (an electric signal) output from an imaging device (not illustrated in the drawings) of the endoscope camera head 5, into an optical signal, and outputs the optical signal to the composite cable 65 (plural second optical fibers 651) via first optical fibers 6322 and the first optical connectors 66. Furthermore, the first photoelectric composite module 63 relays a control signal or the like (an electric signal) output from the control device 9, via the second photoelectric composite module 64 and the composite cable 65, to the hermetic connector 50 provided in the endoscope camera head 5. The first photoelectric composite module 63 includes a receptacle 631, a first substrate 632, two second substrates 633, a holding portion 634, and the first optical connectors 66.

The receptacle 631 is formed of a round connector mechanically and electrically connected to the hermetic connector 50, and is provided at a distal end of the first photoelectric composite module 63. The receptacle 631 has an insulator 6311 formed of an insulating material, and plural contacts 6312. The insulator 6311 has, formed therein, plural insertion holes 6311a where plural conduction pins 501 of the hermetic connector 50 are insertable when the receptacle 631 is connected to the hermetic connector 50. Furthermore, the insulator 6311 has the plural contacts 6312 respectively provided at a proximal end side of the plural insertion holes 6311a. When the plural conduction pins 501 of the hermetic connector 50 are respectively inserted in the plural insertion holes 6311a, the plural contacts 6312 are electrically connected to the plural conduction pins 501.

The first substrate 632 is formed of a rigid substrate, and has, mounted thereon: an E/O converting unit 6321 that converts an electric signal into an optical signal; and the holding portion 634 (see FIG. 2) that holds the first optical connectors 66. The first substrate 632 is electrically connected to plural first contacts 6312a of the receptacle 631, and relays an imaging signal (an electric signal) output from the imaging device (not illustrated in the drawings) of the endoscope camera head 5 via the plural conduction pins 501 and the plural first contacts 6312a, to the E/O converting unit 6321. The E/O converting unit 6321 has the plural first optical fibers 6322 connected thereto. The E/O converting unit 6321 converts the imaging signal (the electric signal) into an optical signal, and outputs the optical signal to the plural first optical fibers 6322. One end of the plural first optical fibers 6322 is connected to the E/O converting unit 6321, and first ferrules 661 that function as a part of the first optical connectors 66 are provided at the other end of the plural first optical fibers 6322. The plural first optical fibers 6322 are optically connected to second ferrules 662 provided at one end of the plural second optical fibers 651 via the first ferrules 661. The holding portion 634 holds the plural first optical connectors 66 optically connected by use of split sleeves 663. A detailed configuration of the holding portion 634 will be described later.

Each of the second substrates 633 is formed of a flexible substrate, at least a part of the flexible substrate being bendable, and has, mounted thereon, a first pin socket 6331 (a connecting portion) that electrically and mechanically connects plural metal cables 652 included in the composite cable 65 to the second substrate 633. Each of the second substrates 633 relays a control signal or the like (an electric signal) output from the control device 9, to plural second contacts 6312b, via the plural metal cables 652 and connectors 6521. That is, the control signals or the like (the electric signals) relayed to the plural second contacts 6312b are output to the imaging device (not illustrated in the drawings) of the endoscope camera head 5 via the plural conduction pins 501. These two second substrates 633 have the same configuration. Furthermore, the two second substrates 633 and the first substrate 632 are three-dimensionally arranged in a state where parts of the two second substrates 633 and first substrate 632 are respectively positioned on different planes and parts of the two second substrates 633 and first substrate 632 overlap one another. The first pin socket 6331 (a female-type socket) is mounted on the second substrate 633 by means of solder or the like.

The first optical connectors 66 optically connect the plural first optical fibers 6322 and the plural second optical fibers 651 respectively to each other. Each of the first optical connectors 66 has: the first ferrule 661 provided in the first optical fiber 6322; a second ferrule 662 provided at one end of the second optical fiber 651; and the split sleeve 663 that connects the first ferrule 661 and the second ferrule 662 to each other.

Configuration of Composite Cable

Described next is a configuration of the composite cable 65.

The composite cable 65 is formed of the plural second optical fibers 651 that transmit optical signals, and the plural metal cables 652 that transmit electric signals, the plural second optical fibers 651 and the plural metal cables 652 having been formed into a unit. Furthermore, both ends of the composite cable 65 each have a GND connector 69 that prevents the composite cable 65 from being bent and functions as earth. A detailed configuration of the GND connector 69 will be described later. At one end of the plural second optical fibers 651, the second ferrules 662 that function as the first optical connectors 66 are provided, and at the other end of the plural second optical fibers 651, third ferrules 671 that function as the second optical connectors 67 are provided. Furthermore, the connectors 6521 (male-type) connectable to the first pin socket 6331 and a second pin socket 6412 are provided at both ends of each of the plural metal cables 652.

Configuration of Second Photoelectric Composite Module

Described next is a configuration of the second photoelectric composite module 64.

The second photoelectric composite module 64 is mechanically, electrically, and optically connected to a receptacle (not illustrated in the drawings) provided in the control device 9. The second photoelectric composite module 64 relays a control signal or the like (an electric signal) output from the control device 9, to the composite cable 65 (the plural metal cables 652). Furthermore, the second photoelectric composite module 64 relays an optical signal output from the first photoelectric composite module 63, to the control device 9 via the composite cable 65. The second photoelectric composite module 64 includes a third substrate 641; a fourth substrate 642, a connector plug 643, a collimator unit 644, third optical fibers 645, and the second optical connectors 67.

The third substrate 641 is arranged in the sheath 68 and formed of a rigid substrate. The third substrate 641 has, mounted thereon: a holding portion 634 (see FIG. 2) that holds the second optical connectors 67; the second pin socket 6412 (a female-type socket) that electrically and mechanically connects the connectors 6521 (male-type) of the plural metal cables 652 to the third substrate 641; and a substrate connector 6413 for electrically connecting the third substrate 641 to the fourth substrate 642. Each of the second pin socket 6412 and substrate connector 6413 is mounted on the third substrate 641 by means of solder or the like. A detailed configuration of the holding portion 634 will be described later.

The fourth substrate 642 is arranged inside the sheath 68 (film) and formed of a rigid substrate. The fourth substrate 642 relays between: plural connector plug electrodes 6431 provided in the connector plug 643; and the third substrate 641. Furthermore, the fourth substrate 642 has an insertion hole 6422 where the plural third optical fibers 645 are inserted. The fourth substrate 642 is electrically connected to each of the plural connector plug electrodes 6431 (plug electric contacts), and is electrically connected to the third substrate 641 via the substrate connector 6413.

The third optical fibers 645 are connected to the collimator unit 644, and the collimator unit 644 forms light (optical signals) emitted from an emission end of the third optical fibers 645 into parallel light.

The second optical connectors 67 optically connect the plural second optical fibers 651 and the plural third optical fibers 645 respectively to each other. Each of the second optical connectors 67 has: the third ferrule 671 provided in the second optical fiber 651; a fourth ferrule 672 provided in the third optical fiber 645; and a split sleeve 673 that connects the third ferrule 671 and the fourth ferrule 672 to each other.

Configuration of Holding Portion

Described next is the detailed configuration of the above described holding portion 634.

Figure 4:
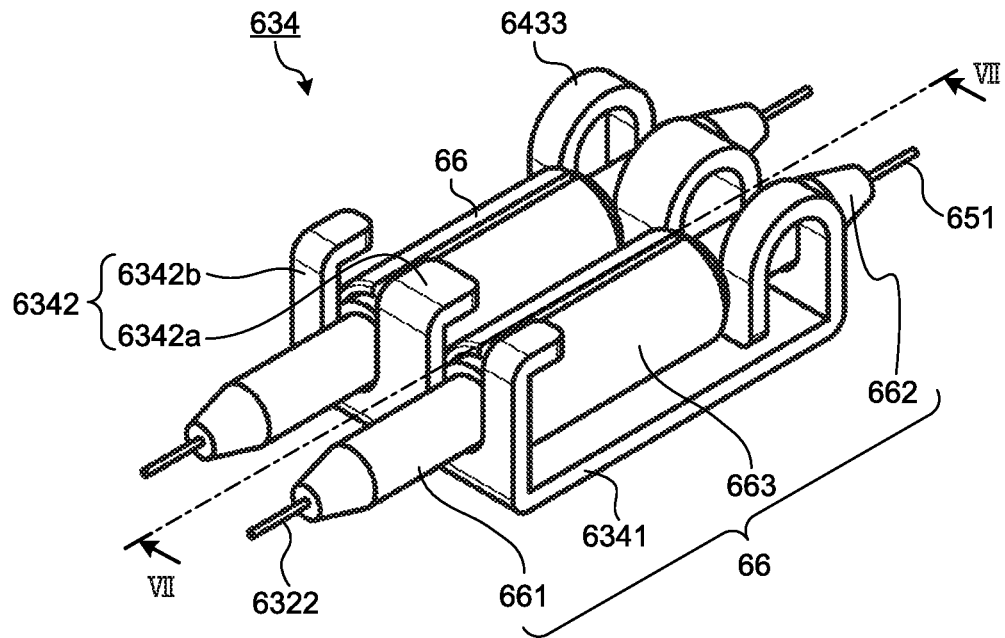
FIG. 4 is a perspective view of a holding portion in FIG. 2 as viewed from a distal end side thereof.
Figure 5:
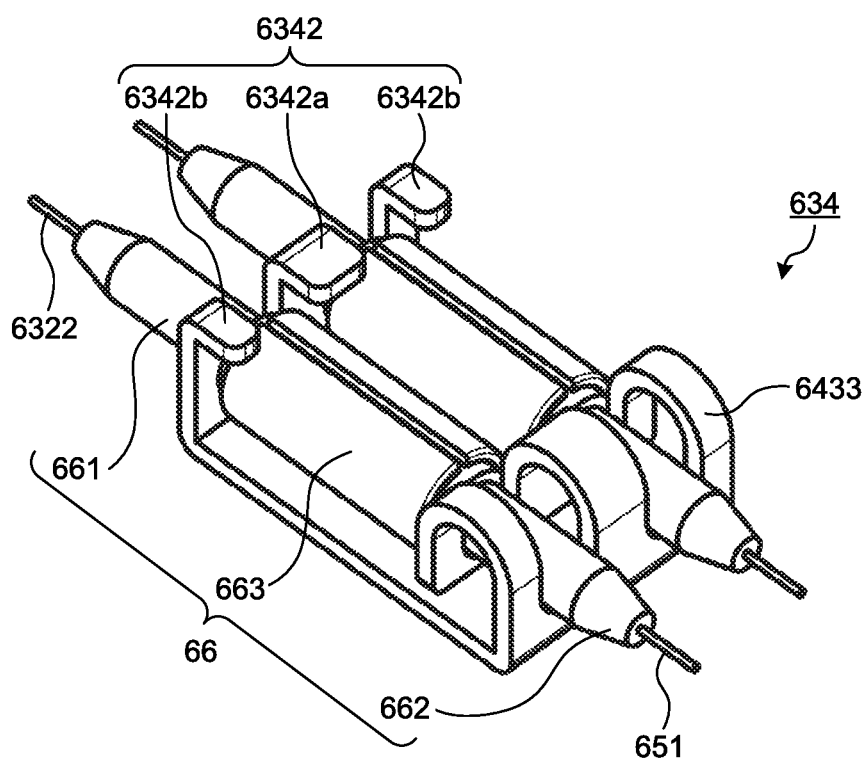
FIG. 5 is a perspective view of the holding portion in FIG. 2 as viewed from a proximal end side thereof.
Figure 6:
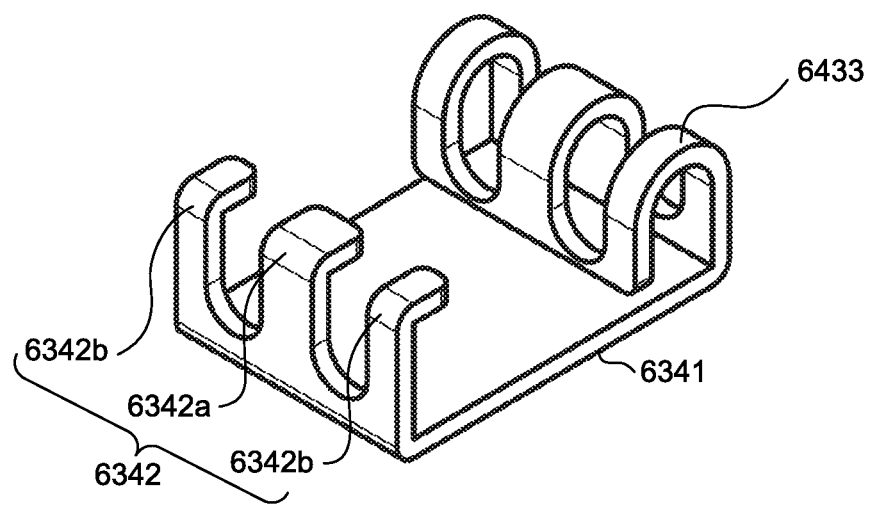
FIG. 6 is a perspective view of only the holding portion in FIG. 2.
Figure 7:
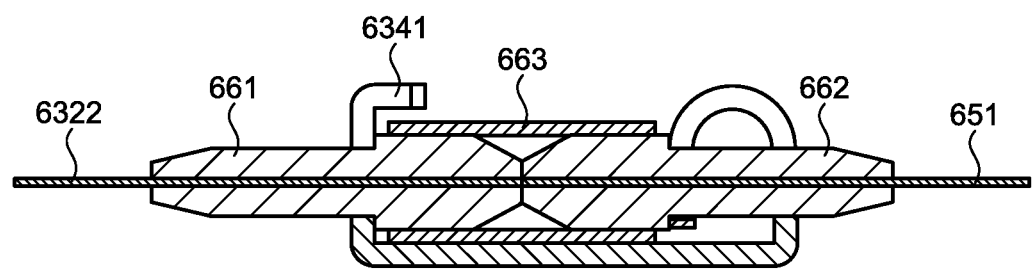
FIG. 7 is a sectional view along a line VII-VII in FIG. 4.

FIG. 4 is a perspective view of the holding portion 634 in FIG. 2 as viewed from a distal end side thereof (from the endoscope camera head 5 side). FIG. 5 is a perspective view of the holding portion 634 in FIG. 2 as viewed from a proximal end side thereof. FIG. 6 is a perspective view of only the holding portion 634 in FIG. 2. FIG. 7 is a sectional view along a line VII-VII in FIG. 4. With respect to FIG. 4 to FIG. 7, a state where the holding portion 634 is holding the first optical connectors 66 will be described, but the same applies to a case where the holding portion 634 holds the second optical connectors 67.

As illustrated in FIG. 4 to FIG. 7, the holding portion 634 holds the plural first optical connectors 66 or the plural second optical connectors 67. The holding portion 634 has a principal surface 6341, plural hook portions 6342, and plural spring portions 6433. The principal surface 6341, the plural hook portions 6342, and the plural spring portions 6433 are integrally formed with one another.

Each of the plural hook portions 6342 is formed by: being extended from a longitudinal direction end portion of the principal surface 6341 in a direction orthogonal to a placement surface where the principal surface 6341 has been placed; and being bent at substantially right angles toward the principal surface 6341. The plural hook portions 6342 are provided at predetermined intervals, and a center hook portion 6342a is formed more largely in width than both end hook portions 6342b. Specifically, the plural hook portions 6342 are each formed to have a width that is substantially the same as a diameter of the first ferrule 661, and are provided at intervals each having a width smaller than a diameter of the split sleeve 663. FIG. 4 to FIG. 7 illustrate an example where three of the hook portions 6342 have been provided for the principal surface 6341, but the number of the hook portions 6342 may be modified as appropriate according to the number of the first optical connectors 66 to be held, without being limited to this example.

Each of the plural spring portions 6433 is formed by: being extended from a longitudinal direction end portion of the principal surface 6341 in a direction orthogonal to the placement surface where the principal surface 6341 has been placed; and being curved toward the principal surface 6341. The plural spring portions 6433 bias the first optical connectors 66 to the hook portions 6342 when the first optical connectors 66 have been accommodated in the holding portion 634.

After a distal end side (the first ferrules 661) of the first optical connectors 66 has been inserted in the hook portions 6342 firstly; the first optical connectors 66 are accommodated in the holding portion 634 that has been formed as described above, by a rear end side of the first optical connectors 66 being pressed by the spring portions 6433 while being abutted by the spring portions 6433. Thereby, the holding portion 634 is able to prevent the first optical connectors 66 from being removed from the holding portion 634 because the spring portions 6433 bias the first optical connectors 66 to the hook portions 6342.

Configuration of GND Connector

Described next is the detailed configuration of the GND connectors 69 described above with respect to FIG. 2.

Figure 8:
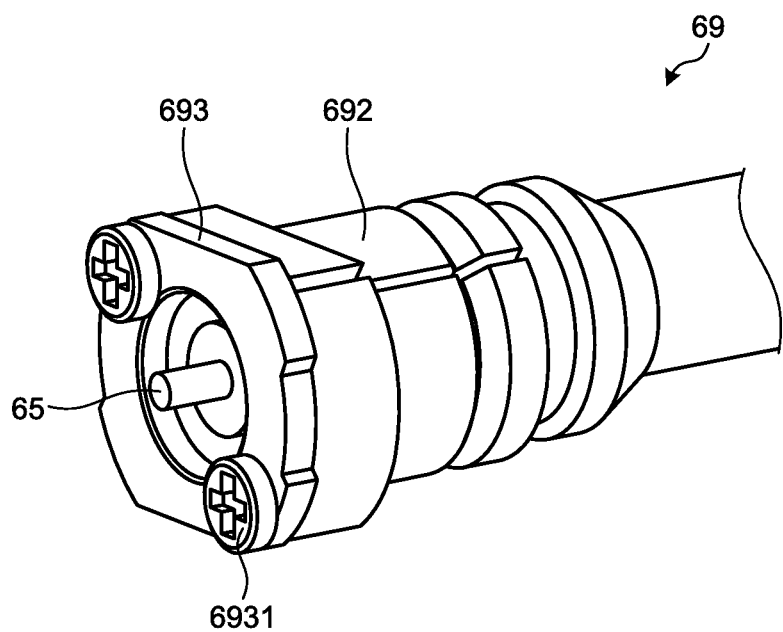
FIG. 8 is a perspective view of a GND connecter in FIG. 2 as viewed from a distal end side thereof.
Figure 9:
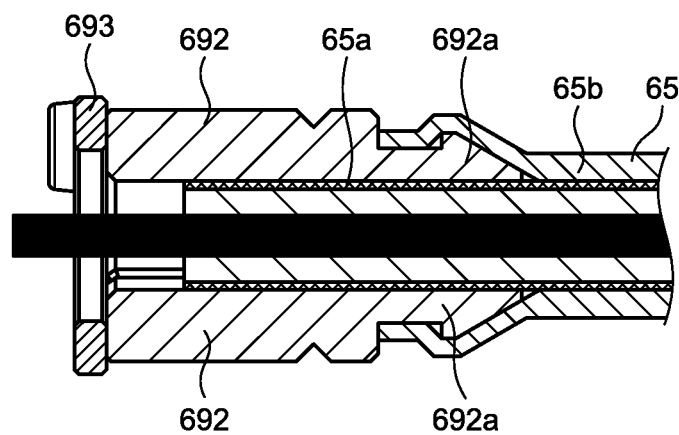
FIG. 9 is a side view of the GND connector in FIG. 2.
Figure 10:
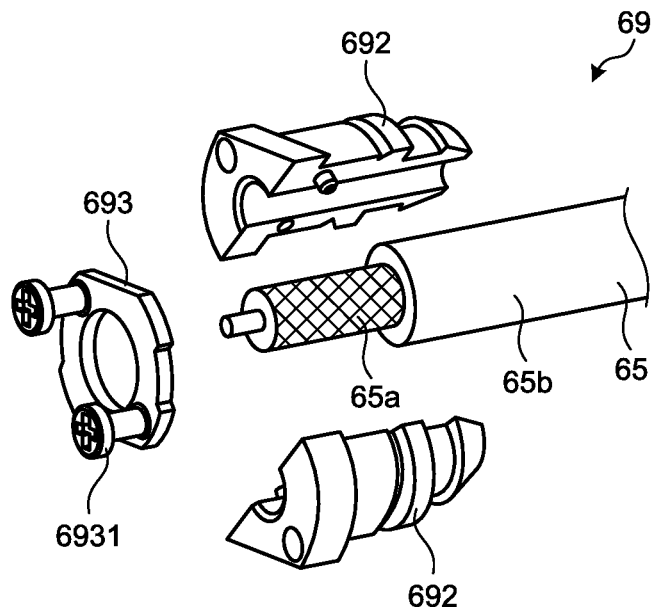
FIG. 10 is a perspective view of a state where the GND connecter in FIG. 8 has been divided.
Figure 11:
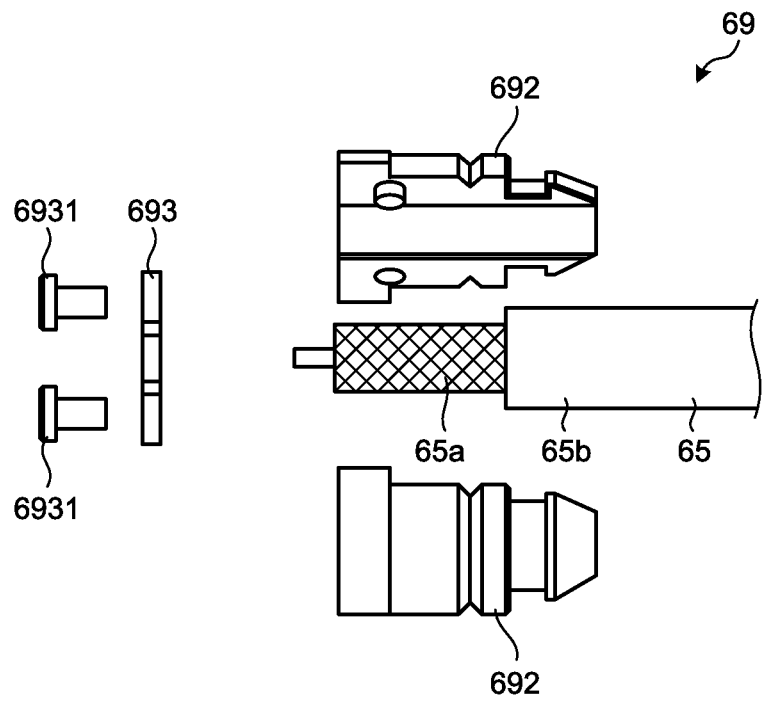
FIG. 11 is a side view of a state where the GND connecter in FIG. 9 has been divided.

FIG. 8 is a perspective view of the GND connector 69 in FIG. 2 as viewed from a distal end side thereof (from the endoscope camera head 5 side). FIG. 9 is a side view of the GND connector 69 in FIG. 2. FIG. 10 is a perspective view of a state where the GND connecter 69 in FIG. 8 has been divided. FIG. 11 is a side view of the state where the GND connecter 69 in FIG. 9 has been divided.

The GND connector 69 has: divided portions 692 that hold the composite cable 65 by having, inserted therebetween, a braided wire 65a of the composite cable; and a binding portion 693 that binds the divided portions 692 together. The divided portions 692: are able to be divided as illustrated in FIG. 10 and FIG. 11; are formed of a conductive material; and have the same potential as the braided wire 65a caused to function as ground, by holding the braided wire 65a of the composite cable 65 therein. A retaining portion 692a that is convex is provided at an end portion of each of the divided portions 692. The composite cable 65 is prevented from coming off from the divided portions 692 by: installation of a sheath 65b of the composite cable 65 to cover the retaining portion 692a by insertion of the retaining portion 692a between the braided wire 65a of the composite cable 65 and the sheath 65b. The binding portion 693 is substantially annular, and a part of the composite cable 65 is inserted in the binding portion 693.

In the GND connector 69 configured as described above: firstly, the braided wire 65a of the composite cable 65 is inserted between the pair of divided portions 692, the braided wire 65a having been exposed from the sheath 65b of the composite cable 65; and the pair of divided portions 692 is attached to the composite cable 65 such that the pair of divided portions 692 is covered by the sheath 65b of the composite cable 65. Thereafter, the binding portion 693 is fixed to the pair of divided portions 692 by screws 6931. Fixing is thereby enabled without consideration of the sequence of assembly of parts to be attached to the front and rear of the GND connector 69, for example, ferrules and split sleeves.

Method of Manufacturing First Transmission Cable

Described next is a method of manufacturing the above described first transmission cable 6.

Figure 12A:
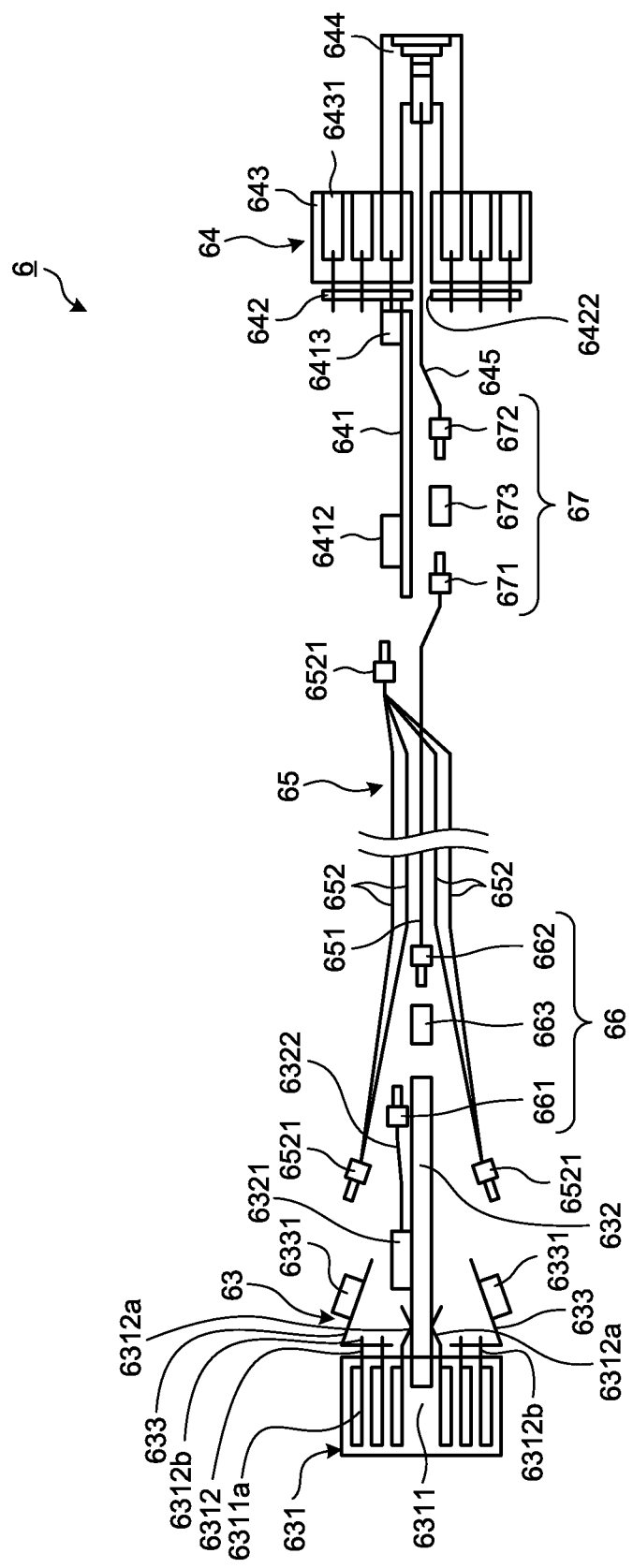
FIG. 12A is a diagram schematically illustrating main parts in a method of manufacturing the first transmission cable according to the first embodiment of the present invention.
Figure 12B:
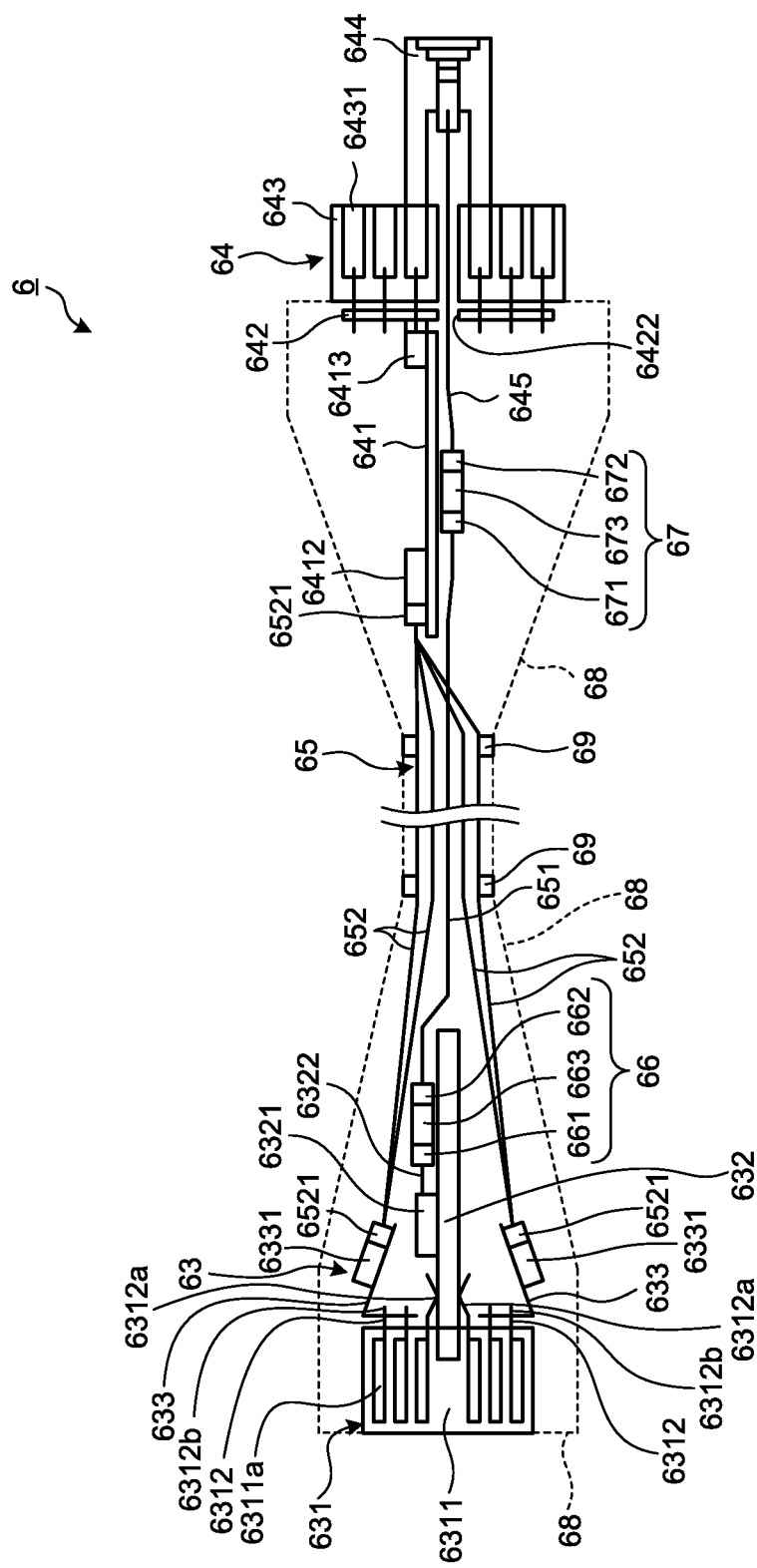
FIG. 12B is a diagram schematically illustrating the main parts in the method of manufacturing the first transmission cable according to the first embodiment of the present invention.
Figure 12C:
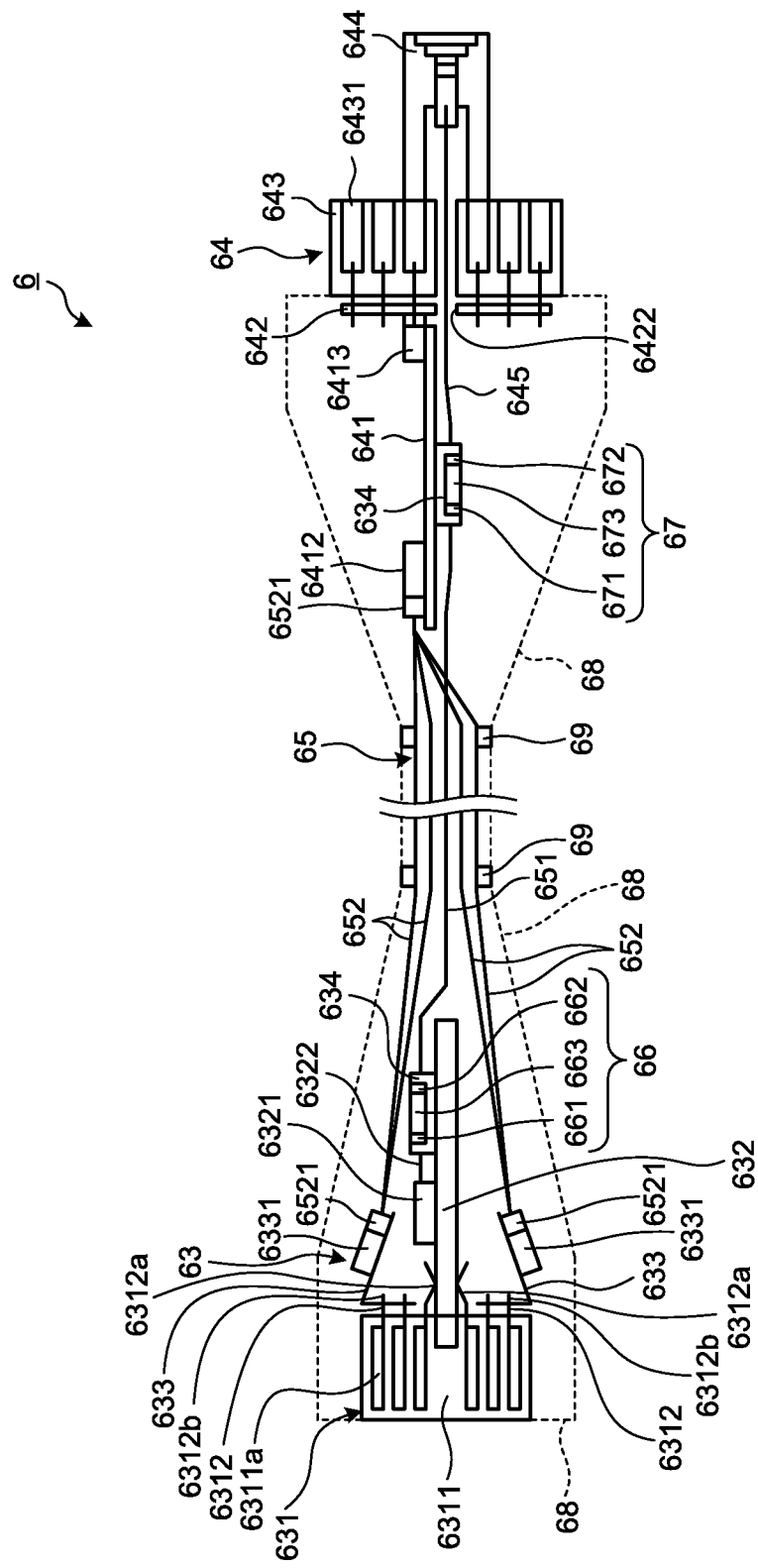
FIG. 12C is a diagram schematically illustrating the main parts in the method of manufacturing the first transmission cable according to the first embodiment of the present invention.

FIG. 12A to FIG. 12C are diagrams schematically illustrating main parts in the method of manufacturing the first transmission cable 6.

As illustrated in FIG. 12A, firstly, an operator connects the composite cable 65 to each of the first photoelectric composite module 63 and the second photoelectric composite module 64 (FIG. 12A-FIG. 12B). For example, the operator optically connects the first ferrules 661 of the first photoelectric composite module 63 and the second ferrules 662 of the second optical fibers 651 in the composite cable 65 to each other by means of the split sleeves 663. Specifically, the operator carries out a butting process (a first butting process) of butting up the centers of the first ferrules 661 and the centers of the second ferrules 662 against each other in the split sleeves 663.

Subsequently, the operator connects the connectors 6521 of the metal cables 652 to the first pin socket 6331 of the first photoelectric composite module 63 (a first connection process).

Thereafter, the operator connects the second photoelectric composite module 64 and the composite cable 65 to each other. Specifically, the operator optically connects the fourth ferrule 672 of the second photoelectric composite module 64 and the third ferrule 671 of the composite cable 65 to each other by means of the split sleeve 673. Specifically, the operator carries out a butting process of butting up the center of the third ferrule 671 and the center of the fourth ferrule 672 against each other in the split sleeve 673 (a second butting process).

Subsequently, the operator connects the connectors 6521 of the metal cables 652 to the second pin socket 6412 of the second photoelectric composite module 64 (a second connection process).

Thereafter, the operator makes the holding portions 634 accommodate therein the first optical connectors 66 and the second optical connectors 67, and places the holding portion 634 respectively on the first substrate 632 and the third substrate 641 (FIG. 12B-FIG. 12C) (a holding process).

The operator then connects the GND connectors 69 to the composite cable 65 and covers the composite cable 65 with the sheath 68 (a covering process).

According to the above described first embodiment, even if optical fibers are used, improved cost performance is achieved.

Furthermore, according to the first embodiment, since the first transmission cable 6 has, built therein, the first optical fibers 6322, the second optical fibers 651, the first optical connectors 66 that connect the first optical fibers 6322 and the second optical fibers 651 to each other, the third optical fibers 645, and the second optical connectors 67 that connect the second optical fibers 651 and the third optical fibers 645 to each other; alignment with the optical axis of the E/O converter or O/E converter is able to be carried out easily, and disconnection of the optical fibers upon connection of the optical fibers to the E/O converting unit 6321 is able to be prevented.

Furthermore, according to the first embodiment, since the optical fibers are not required to be sent to manufacturers of the converters or the like, the economical cost is able to be reduced.

Furthermore, according to the first embodiment, since the first transmission cable 6 has, built therein, the first optical fibers 6322, the second optical fibers 651, the first optical connectors 66 that connect the first optical fibers 6322 and the second optical fibers 651 to each other, the third optical fibers 645, and the second optical connectors 67 that connect the second optical fibers 651 and the third optical fibers 645 to each other; if, for example, any of the second optical fibers 651 is disconnected and the first transmission cable 6 is to be replaced with a new first transmission cable 6, optical fibers are optically connected by use of first optical connectors 66 and second optical connectors 67, and thus the replacement is facilitated.

Furthermore, according to the first embodiment, since the plural metal cables 652 that transmit electric signals and the second optical fibers 651 are formed into a unit that functions as the composite cable 65, the first transmission cable 6 is able to be handled easily.

Furthermore, according to the first embodiment, by provision of the first pin socket 6331 and the second pin socket 6412 respectively on the second substrate 633 and the third substrate 641, provision of the connectors 6521 at both ends of the plural metal cables 652, and making the first pin socket 6331, the second pin socket 6412, and the connectors 6521 function as cable connectors; the soldering process for the metal cables 652 is able to be omitted and the assembly is facilitated.

Furthermore, according to the first embodiment, by forming each of the first photoelectric composite module 63, second photoelectric composite module 64, and composite cable 65 of the first transmission cable 6 into a module, the connection process between the E/O converting unit 6321 and optical fibers, and the connection process between the collimator unit 644 and optical fibers do not need to be combined in sequence, the connection processes are able to be performed as independent processes, and thus the manufacturing time is able to be shortened, spoilage expenses are able to be cut, and the final assembly processing is able to be simplified.

Figure 13:
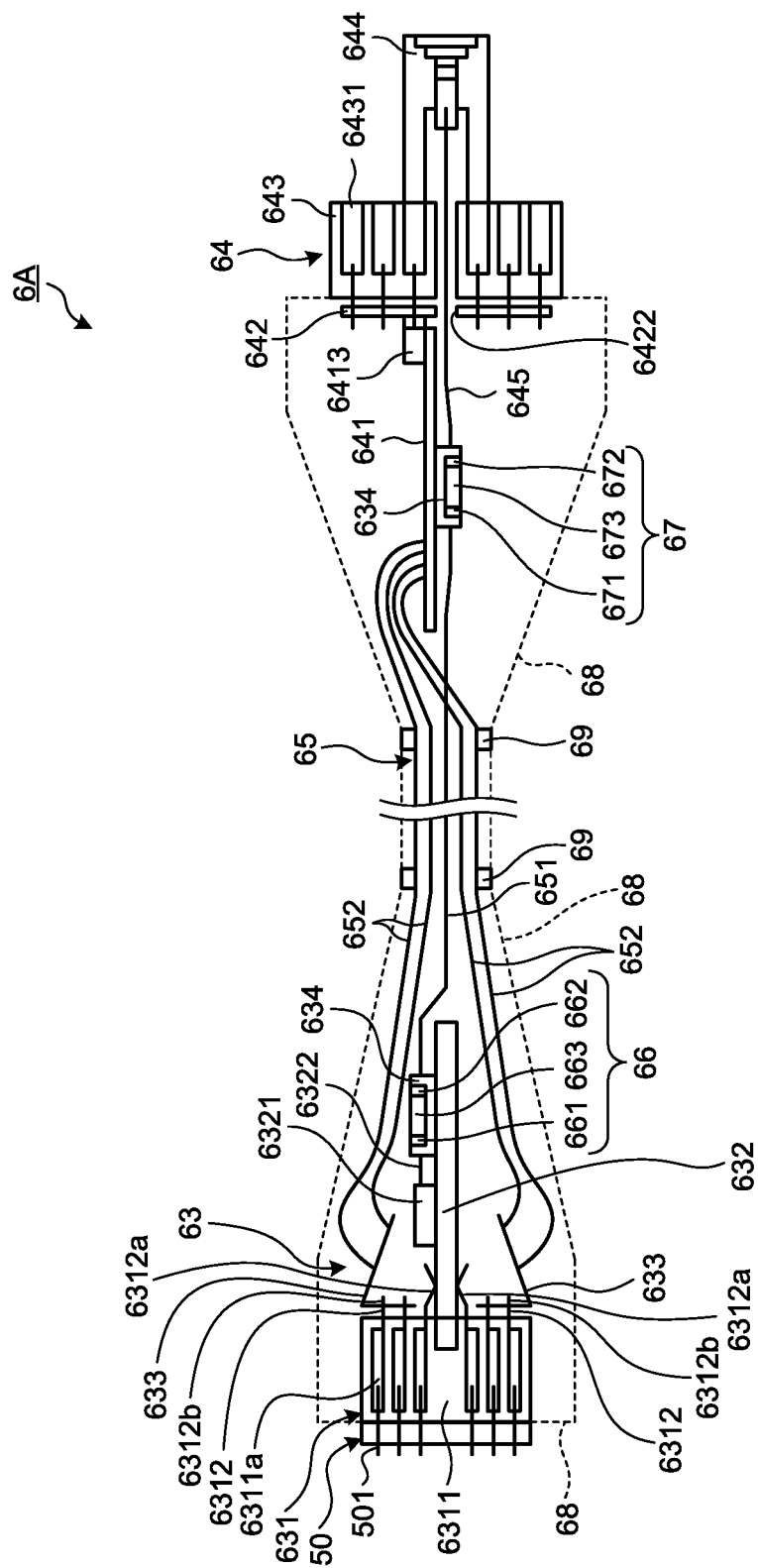
FIG. 13 is a schematic diagram illustrating a cross section of another first transmission cable according to the first embodiment of the present invention.

According to the first embodiment, connection is achieved by the provision of the connectors 6521 at both ends of the plural metal cables 652 and provision of the first pin socket 6331 on the second substrate 633 and the second pin socket 6412 on the third substrate 641, but the first embodiment is not limited to this connection, and as exemplified by a first transmission cable 6A illustrated in FIG. 13, both ends of each of the plural metal cables 652 and the second substrate 633 and the third substrate 641 may be respectively connected to each other by soldering.

Figure 14:
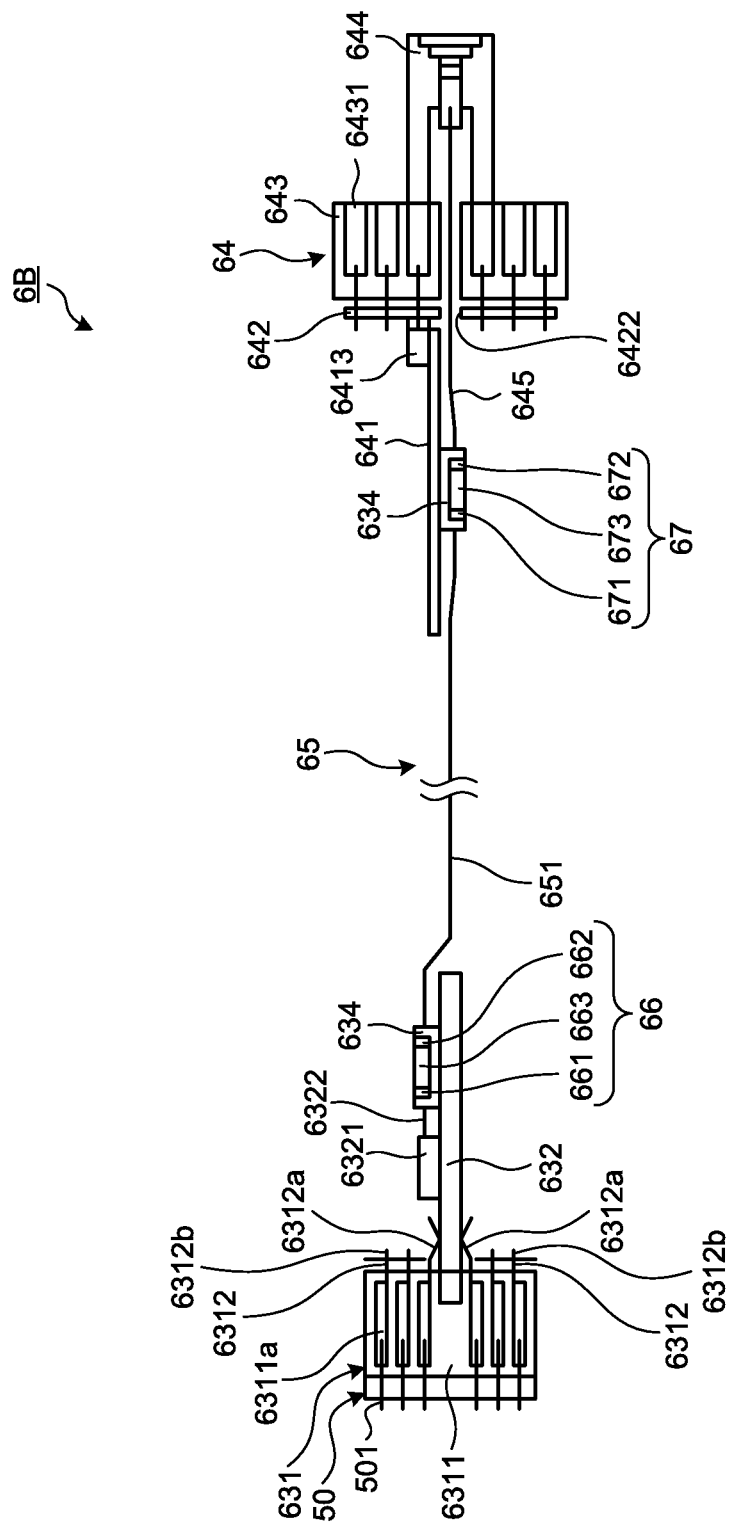
FIG. 14 is a schematic diagram illustrating another first transmission cable according to the first embodiment of the present invention.

Furthermore, according to the first embodiment, a control signal (an electric signal) from the control device 9 is transmitted to the endoscope camera head 5 through the plural metal cables 652, but as exemplified by a first transmission cable 6B illustrated in FIG. 14, the control signal may be transmitted through plural optical fibers, instead of the plural metal cables 652.

According to the first embodiment, the control device 9 is optically connected by use of the collimator unit 644, but, for example, an O/E converter may be provided on the third substrate 641, an optical signal may be converted to an electric signal, and the electric signal may be output to the control device 9. In this case, the third optical fibers 645 may be provided in the O/E converter and optically connected to the second optical fibers 651 by use of the second optical connectors 67, and the O/E converter and the connector plug 643 may be electrically connected to each other via the substrate connector 6413.

Second Embodiment

Described next is a second embodiment of the present invention. According to the above described first embodiment, the present invention is applied to the medical apparatus having the rigid scope (the insertion unit 2) used therein, but according to the second embodiment, the present invention is applied to a medical observation system having a flexible endoscope used therein, the flexible endoscope having an imaging unit at a distal end of an insertion unit thereof and being a so-called video scope. Any component that is the same as that of the above described first embodiment will be assigned with the same reference sign, and detailed description thereof will be omitted or simplified.

Figure 15:
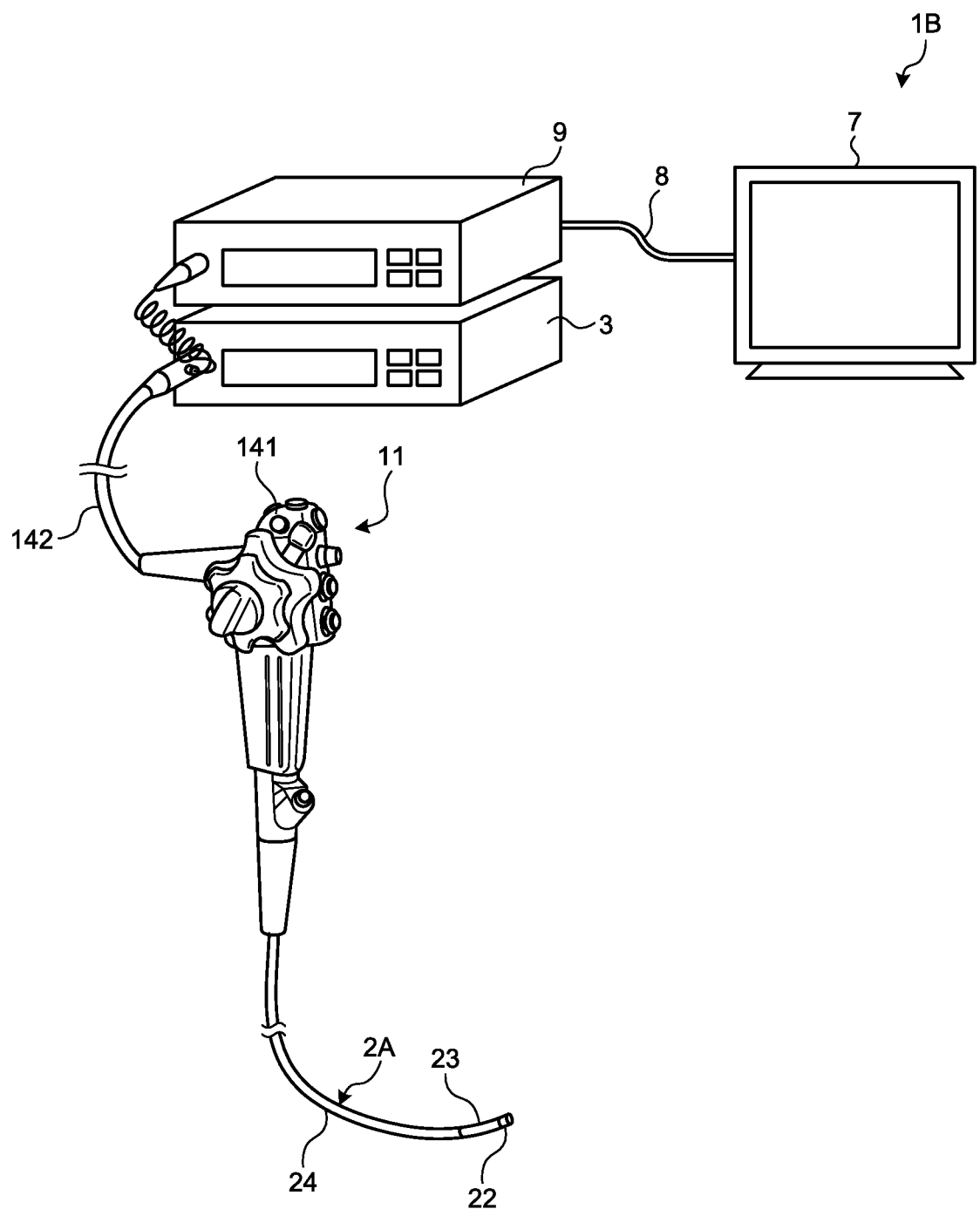
FIG. 15 is a diagram illustrating a schematic configuration of a medical apparatus according to a second embodiment of the present invention.

FIG. 15 is a diagram illustrating a schematic configuration of a medical apparatus according to the second embodiment. A medical apparatus 1B illustrated in FIG. 15 includes: an endoscope 11 that captures an in-vivo image of an observed region of a subject by insertion of an insertion unit 2A into a living body and outputs an image signal; a light source device 3 that generates illumination light to be emitted from a distal end of the endoscope 11; the control device 9 that processes the image signal output from the endoscope 11, and generates and outputs a video signal; and the display device 7 that displays thereon an image based on the video signal.

The endoscope 11 includes, as illustrated in FIG. 15: the insertion unit 2A having flexibility and an elongated shape; an operating unit 141 that is connected to a proximal end of the insertion unit 2A and receives input of various operation signals; and a universal cord 142 that extends in a direction different from a direction, in which the insertion unit 2A extends from the operating unit 141, is connected to the light source device 3 and control device 9, and that has, built therein, various cables including the above described first transmission cable 6.

The insertion unit 2A includes, as illustrated in FIG. 15: a distal end portion 22 having, built therein, an imaging unit (not illustrated in the drawings) that captures an in-vivo image of a living body and generates an image signal; a bending portion 23 that is connected to a proximal end of the distal end portion 22, is formed of plural bending pieces, and is bendable; and a flexible tube portion 24 that is connected to a proximal end of the bending portion 23, has flexibility, and has a long shape. The image signal captured by the distal end portion 22 (the imaging unit) is output to the control device 9 via the operating unit 141 and the universal cord 142 having, built therein, the above described first transmission cable 6.

According to the above described second embodiment, even if the flexible endoscope (the endoscope 11) is used, effects similar to those of the above described first embodiment are achieved.

Third Embodiment

Described next is a third embodiment of the present invention. According to the above described first embodiment, the present invention is applied to the medical apparatus 1 having the rigid scope (the insertion unit 2) used therein, but according to the third embodiment, the present invention is applied to a medical apparatus having a surgical microscope used therein, the surgical microscope capturing an enlarged image of a predetermined field area inside a subject (in a living body) or on a surface of the subject (on a surface of the living body). In the following description, any component that is the same as that of the above described first embodiment will be assigned with the same reference sign, and detailed description thereof will be omitted or simplified.

Figure 16:
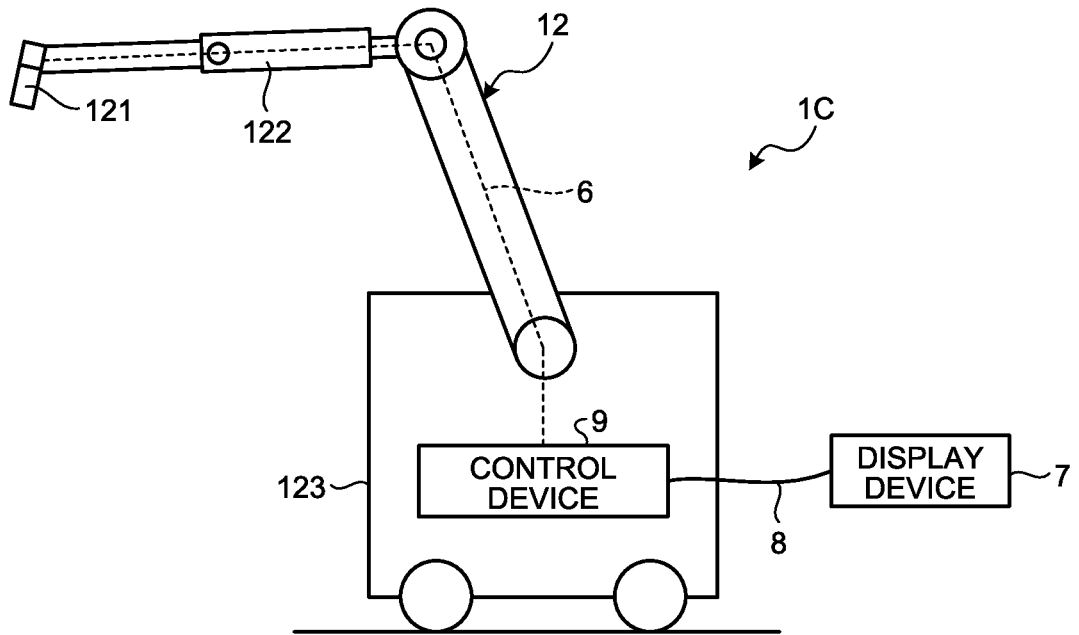
FIG. 16 is a diagram illustrating a schematic configuration of a medical apparatus according to a third embodiment of the present invention.

FIG. 16 is a diagram illustrating a schematic configuration of the medical apparatus according to the third embodiment. A medical apparatus 1C illustrated in FIG. 16 includes: a surgical microscope 12 that captures an image of a subject and outputs an image signal; the control device 9 that processes the image signal output from the surgical microscope 12 and generates and outputs a video signal; and the display device 7 that displays thereon an image based on the video signal.

The surgical microscope 12 includes, as illustrated in FIG. 16: a microscope unit 121 that captures an enlarged image of a micro region of a subject and outputs an image signal; a supporting portion 122 that is connected to a proximal end portion of the microscope unit 121 and includes an arm that supports the microscope unit 121 turnably; and a base unit 123 that holds a proximal end portion of the supporting portion 122 turnably and is movable on a floor surface.

The control device 9 is arranged, as illustrated in FIG. 16, in the base unit 123. Furthermore, the supporting portion 122 has the first transmission cable 6 arranged along the supporting portion 122. That is, the image signal captured by the microscope unit 121 is output to the control device 9 via the first transmission cable 6.

Instead of being provided movably on the floor surface, the base unit 123 may be configured to support the supporting portion 122 by being fixed to a ceiling, a wall surface, or the like. Furthermore, the base unit 123 may include a light source unit that generates illumination light to be emitted from the surgical microscope 12 to a subject.

According to the above described third embodiment, even if the surgical microscope 12 is used, effects similar to those of the above described first embodiment are achieved.

Figure 17:
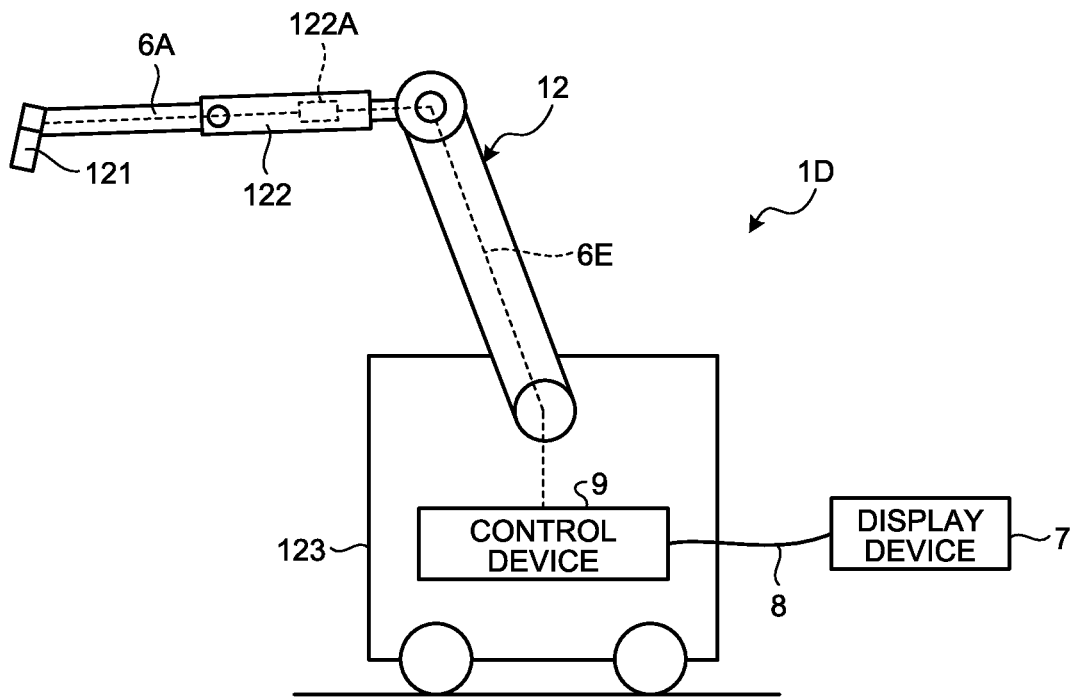
FIG. 17 is a diagram illustrating a schematic configuration of another medical apparatus according to the third embodiment of the present invention.

According to the third embodiment, the microscope unit 121 and the control device 9 are optically and electrically connected to each other through the first transmission cable 6; but like a medical apparatus 1D illustrated in FIG. 17, a relay device 122A may be provided between the microscope unit 121 and the control device 9, the microscope unit 121 and the relay device 122A may be optically and electrically connected to each other through the first transmission cable 6A having the same configuration as the above described first transmission cable 6, and the relay device 122A and the control device 9 may be optically and electrically connected to each other through a transmission cable 6E having the same configuration as the above described first transmission cable 6. Of course, the microscope unit 121 and the relay device 122A may be optically connected to each other through the optical fibers and optical connectors illustrated in FIG. 14.

Other Embodiments

In the description of the method of manufacturing the medical apparatus in this specification, the context of the processes is disclosed by use of expressions, such as "firstly", "thereafter", and "subsequently", but sequences of the processes necessary for carrying out the present invention are not uniquely defined by these expressions. That is, the sequences of the processes in the method of manufacturing the medical apparatus described in this specification may be modified as far as no contradiction arises from the modification.

As described above, the present invention may include various embodiments not described herein, and various design changes and the like may be carried out within the scope of the technical ideas determined by the claims.

REFERENCE SIGNS LIST 1, 1B, 1C, 1D MEDICAL APPARATUS
2, 2A INSERTION UNIT
3 LIGHT SOURCE DEVICE
4 LIGHT GUIDE
5 ENDOSCOPE CAMERA HEAD
6, 6A, 6B FIRST TRANSMISSION CABLE
7 DISPLAY DEVICE
8 SECOND TRANSMISSION CABLE
9 CONTROL DEVICE
10 THIRD TRANSMISSION CABLE
11 ENDOSCOPE
12 SURGICAL MICROSCOPE
21 EYEPIECE UNIT
22 DISTAL END PORTION
23 BENDING PORTION
24 FLEXIBLE TUBE PORTION
50 HERMETIC CONNECTOR
61 VIDEO CONNECTOR
62 CAMERA HEAD CONNECTOR
63 FIRST PHOTOELECTRIC COMPOSITE MODULE
64 SECOND PHOTOELECTRIC COMPOSITE MODULE
65 COMPOSITE CABLE
66 FIRST OPTICAL CONNECTOR
67 SECOND OPTICAL CONNECTOR
68 SHEATH
69 GND CONNECTOR
121 MICROSCOPE UNIT
122 SUPPORTING PORTION
122A RELAY DEVICE
123 BASE UNIT
632 FIRST SUBSTRATE
633 SECOND SUBSTRATE
634 HOLDING PORTION
641 THIRD SUBSTRATE
642 FOURTH SUBSTRATE
645 THIRD OPTICAL FIBER
651 SECOND OPTICAL FIBER
652 METAL CABLE
661 FIRST FERRULE
662 SECOND FERRULE
663, 673 SPLIT SLEEVE
671 THIRD FERRULE
672 FOURTH FERRULE
692 DIVIDED PORTION
693 BINDING PORTION
6321 E/O CONVERTING UNIT
6322 FIRST OPTICAL FIBER

The invention claimed is:

1. A medical apparatus comprising:
a first optical fiber to transmit an optical signal;
a second optical fiber to transmit the optical signal;
a first substrate;
a first optical connector on the first substrate, the first optical connector to connect the first optical fiber and the second optical fiber;
a composite cable including:
   a metal cable configured to transmit an electric signal, the metal cable having a first electrical connector on a first end and a second electrical connector on a second end, opposite the first end; and
   at least one of the first optical fiber and the second optical fiber, the metal cable and the at least one of the first optical fiber or the second optical fiber forming a unit;
a first cable socket adjacent the first substrate configured to receive the first electrical connector of the metal cable; and
an E/O converter on the first substrate, wherein the E/O converter is connected to a first end of the first optical fiber, the E/O converter being configured to convert an electric signal into the optical signal, wherein
the first optical connector includes a first ferrule on the first substrate and a second ferrule on the first substrate,
a second end of the first optical fiber is in the first ferrule,
a first end of the second optical fiber that faces the second end of the first optical fiber is in the second ferrule,
the first optical fiber and the second optical fiber are optically connected via the first and second ferrules,
a second end of the second optical fiber is to be connected to a second optical connector on a second substrate, separate from the first substrate, the second optical connector to connect second end of the second optical fiber and a third optical fiber to transmit the optical signal, and
the second electrical connector of the metal cable is to be connected to a second cable socket on the second substrate.

2. The medical apparatus according to claim 1, further comprising:
an O/E converter on the second substrate, the O/E converter connected to the third optical fiber, the O/E converter to convert the optical signal into an electric signal.

3. The medical apparatus according to claim 1, further comprising a sheath configured to cover the composite cable.

4. The medical apparatus according to claim 1, further comprising:
a third substrate that overlaps the first substrate, wherein the first cable socket is
on the third substrate.

5. The medical apparatus according to claim 1, wherein the medical apparatus is an endoscope apparatus.

6. The medical apparatus according to claim 1, wherein the medical apparatus is an endoscope camera head.

7. The medical apparatus according to claim 1, wherein the medical apparatus is a surgical microscope.

8. The medical apparatus according to claim 1, wherein the medical apparatus is a transmission cable that has one end connected to an endoscope camera head and another end connected to an image processing device, and is configured to transmit an image signal from the endoscope camera head to the image processing device, the image signal serving as the optical signal.

9. The medical apparatus according to claim 1, further comprising a holder to hold the first optical connector.

10. The medical apparatus according to claim 9, wherein the holder includes a principal surface, at least two hook portions at a first end of the principal surface and at least two spring portions at a second end of the principal surface, opposite the first end.

11. The medical apparatus according to claim 10, wherein the first ferrule is between the at least two hook portions and the second ferrule is between the at least two spring portions.

12. The medical apparatus according to claim 11, further comprising a split sleeve that connects the first and second ferrules.

13. The medical apparatus according to claim 12, wherein the split sleeve extends between the at least two hook portions and the at least two hook portions.

14. The medical apparatus according to claim 9, wherein the first optical connector includes two first ferrules and two second ferrules, the holder includes a principal surface, at least three hook portions at a first end of the principal surface and at least three spring portions at a second end of the principal surface, opposite the first end, wherein a central hook portion of the at least three hook portions has a larger width than other at least three hook portions.

15. The medical apparatus according to claim 1, further comprising a split sleeve that connects the first and second ferrules.

16. A method of manufacturing a medical apparatus including a first optical fiber that transmits an optical signal, a second optical fiber that transmits the optical signal, and a metal cable that transmits an electric signal, d the metal cable having a first electrical connector on a first end and a second electrical connector on a second end, opposite the first end the metal cable and at least one of the first optical fiber or the second optical fiber forming a composite cable as a unit, the method including, inside the medical apparatus:
connecting the first optical fiber and the second optical fiber to each other by using a first optical connector including a first ferrule and a second ferrule on a first substrate;
connecting the first electrical connector of the metal cable in a first cable socket adjacent the first substrate;
connecting an E/O converter on the first substrate, wherein the E/O converter is connected to a first end of the first optical fiber, the E/O converter converting an electric signal into the optical signal;
providing a second end of the first optical fiber in the first ferrule;
providing a first end of the second optical fiber that faces the second end of the first optical fiber in the second ferrule;
optically connecting the first optical fiber and the second optical fiber via the first and second ferrules;
connecting a second end of the second optical fiber to a second optical connector on a second substrate, separate from the first substrate, the second optical connector to connect the second optical fiber and a third optical fiber to transmit the optical signal; and
connecting the second electrical connector of the metal cable to a second cable socket on the second substrate.

17. The method according to claim 16, further comprising:
inserting the first ferrule between hook portions of a holder; and
inserting the second ferrule between spring portions of the holder, the spring portions being on an opposite side of a principal surface of the holder.

18. The method according to claim 17, further comprising butting up centers of the first and second ferrules in a split sleeve.

19. The method according to claim 16, further comprising butting up centers of the first and second ferrules in a split sleeve.

20. A kit for a medical apparatus, the kit comprising:
a first optical fiber that transmits an optical signal;
a second optical fiber that transmits the optical signal;
a metal cable that transmits an electric signal, the metal cable having a first electrical connector on a first end and a second electrical connector on a second end, opposite the first end, the metal cable and at least one of the first optical fiber and the second optical fiber forming a composite cable as a unit;
a first substrate including
a first optical connector, the first optical connector connecting the first optical fiber and the second optical fiber to each other, the first optical connector including a first ferrule on the first substrate and a second ferrule on the first substrate, and
an E/O converter on the first substrate, the E/O converter to be connected to a first end of the first optical fiber, the E/O converter converting an electric signal into the optical signal, wherein
a second end of the first optical fiber to be inserted in the first ferrule,
a first end of the second optical fiber that faces the second end of the first optical fiber to be inserted in the second ferrule;
a first cable socket adjacent the first substrate to be connected with the first electrical connector of the metal cable, and
a second substrate, separate from the first substrate, including a second optical connector and a second cable socket, the second optical connector to connect the second optical fiber and a third optical fiber to transmit the optical signal, the second cable socket on the second substrate is to be connected with the second electrical connector of the metal cable.

* * * * *